(12) United States Patent
Bunke et al.

(10) Patent No.: US 7,290,571 B2
(45) Date of Patent: Nov. 6, 2007

(54) FILLING DEVICE FOR AN ANESTHETIC EVAPORATOR

(75) Inventors: Claus Bunke, Sereetz (DE); Matthias Witt, Bad Schwartau (DE); Rainer Kunz, Lübeck (DE); Jürgen Müller, Lübeck (DE); Sven Heyer, Lübeck (DE); Dirk Reichert, Lübeck (DE)

(73) Assignee: Dräger Medical AG & Co. KGaA (DE)

( * ) Notice: Subject to any disclaimer, the term of this patent is extended or adjusted under 35 U.S.C. 154(b) by 167 days.

(21) Appl. No.: 11/153,310

(22) Filed: Jun. 15, 2005

(65) Prior Publication Data

US 2006/0048842 A1  Mar. 9, 2006

(30) Foreign Application Priority Data

Sep. 9, 2004 (DE) .................. 10 2004 043 652

(51) Int. Cl.
  *B65B 1/04* (2006.01)
(52) U.S. Cl. .................. 141/18; 141/302; 141/351
(58) Field of Classification Search .................. 141/2, 141/18, 301, 302, 351; 128/203.16, 203.12; 137/614.02–614.05; 251/149.1

See application file for complete search history.

(56) References Cited

U.S. PATENT DOCUMENTS

| | | | | |
|---|---|---|---|---|
| 5,505,236 A | * | 4/1996 | Grabenkort et al. | 141/329 |
| 5,617,906 A | * | 4/1997 | Braatz et al. | 141/21 |
| 5,687,777 A | * | 11/1997 | Dobson et al. | 141/18 |
| 6,394,087 B1 | * | 5/2002 | Kankkunen et al. | 128/203.16 |
| 6,708,740 B2 | * | 3/2004 | Wessberg | 141/301 |
| 6,929,041 B2 | * | 8/2005 | Falligant et al. | 141/351 |

FOREIGN PATENT DOCUMENTS

WO   WO96/06301   2/1996

* cited by examiner

*Primary Examiner*—Steven O. Douglas
(74) *Attorney, Agent, or Firm*—McGlew and Tuttle, P.C.

(57) ABSTRACT

A filling device for an anesthetic evaporator has filling of an anesthetic evaporator is possible. To accomplish the object, an additional vent hole (36), which is opened immediately after the filling in order for excess anesthetic volume to be able to flow out of the filling device into the anesthetic tank (15) of the anesthetic evaporator (2), is provided within the filling device above a fluid channel (14), via which both the gas and liquid exchange takes place during the filling.

8 Claims, 5 Drawing Sheets

Prior Art

FILLING DEVICE FOR AN ANESTHETIC EVAPORATOR

CROSS REFERENCE TO RELATED APPLICATIONS

This application claims the benefit of priority under 35 U.S.C. § 119 of German Application DE 10 2004 043 652.5 filed Sep. 9, 2004, the entire contents of which are incorporated herein by reference.

FIELD OF THE INVENTION

The present invention pertains to an anesthetic evaporator.

BACKGROUND OF THE INVENTION

A filling device of this type has become known from WO 96/06301. An anesthetic bottle is provided with a stationary outer tube and an inner tube, which is displaceable in such a way that it can perform a lifting motion and with which a bottle valve on the anesthetic bottle can be opened. A filling device at the anesthetic evaporator has a mounting hole for the outer tube and a stationary inner part, which can be brought into functional connection with the inner tube of the anesthetic bottle. A filling valve of the filling device, which valve is in connection with an anesthetic tank, has a valve plate, which can be lifted off from the valve seat by means of three pins, which point from the valve plate into the mounting hole.

When the anesthetic bottle is being introduced into the filling device, the outer tube will first touch the pins, as a result of which the valve plate of the filling valve is lifted off from the valve seat. The inner part will subsequently come into functional connection with the inner tube of the anesthetic bottle and the bottle valve of the anesthetic bottle opens. During the filling operation, the anesthetic bottle and the anesthetic tank are connected with one another in the form of communicating vessels via a fluid channel at the filling device, via which the liquid and gas exchange takes place.

When the anesthetic tank is filled with anesthetic to the maximum filling level, the filling operation ends due to the closure of the fluid channel, because no liquid or gas exchange is possible any longer between the anesthetic bottle and the anesthetic tank. It may happen now that a residual volume of anesthetic remains in the filling device and cannot flow off into the anesthetic tank any longer. Such residual volumes are problematic especially in case of anesthetics with low boiling points, because they escape directly into the environment after the removal of the anesthetic bottle from the filling device. A pressure, which is released abruptly when the anesthetic bottle is removed from the filling device after the filling, builds up during the filling in both the anesthetic tank and the anesthetic bottle because of the low boiling points of such anesthetics. Residual volumes of anesthetic that may have remained in the filling device may now be entrained to the outside.

SUMMARY OF THE INVENTION

The basic object of the present invention is to provide a device and a process for the improved filling of an anesthetic evaporator.

According to the invention, a filling device for an anesthetic evaporator is designed to receive a connection means of an anesthetic bottle and comprises a filling valve, which is intended to open or close as needed. The anesthetic bottle and an anesthetic tank of the anesthetic evaporator are connected with one another during the filling operation in the form of communicating vessels via a fluid channel that can be closed by the liquid level of the anesthetic in the anesthetic tank. A vent hole, which can be opened or closed as needed is located above the fluid channel. The vent hole is provided, by means of which an additional volume of anesthetic located above the liquid level of the fluid channel can be filled into the anesthetic tank.

According to another aspect of the invention, a process is provided for filling an anesthetic evaporator with an anesthetic bottle via a filling device at the anesthetic evaporator. The process includes inserting the connection means of the anesthetic bottle into a mounting hole at the filling device and opening a filling valve at the filling device. Anesthetic is introduced from the anesthetic bottle into the anesthetic evaporator via a fluid channel at the filling device. An anesthetic tank of the anesthetic evaporator and the anesthetic bottle are connected with one another during the filling operation in the form of communicating vessels. The fluid channel can be closed by the liquid level in the anesthetic tank. A vent hole, which can be opened as needed and with which an additional volume of liquid, which is above the liquid level of the fluid channel, can be filled into the anesthetic tank, is provided above the fluid channel.

The advantage of the present invention is essentially that a vent hole, which is opened immediately after the termination of the filling operation in order to enable excess anesthetic to flow off into the anesthetic tank from the filling device, is arranged above a fluid channel, via which the anesthetic tank is filled with anesthetic. The capacity of the anesthetic tank is increased by the vent hole, so that a residual volume of anesthetic, which has remained in the filling device, can still be taken up.

The anesthetic bottle and the anesthetic tank are connected with one another in the form of communicating vessels during the filling operation. The gas and liquid exchange between the anesthetic bottle and the anesthetic tank takes place via the fluid channel at the filling device. The liquid level in the anesthetic tank rises to the level of the fluid channel. The filling operation is then terminated automatically, because no exchange of gas is possible any longer through the fluid channel. When the user removes the anesthetic bottle from the filling device to the extent that the bottle valve of the anesthetic bottle is just closed, the vent hole is released by a vent valve, so that the residual volume left can flow off from the filling device into the anesthetic tank.

The vent valve is advantageously mechanically connected with the filling valve such that it is switched into the open position immediately after the filling operation, but it is switched into the closed position during the filling operation. The liquid level in the anesthetic tank can thus rise only up to the level of the fluid channel during the filling operation.

Provisions are advantageously made for providing as the vent valve a closing bolt that can be displaced telescopically in relation to the valve plate of the filling valve. The closing bolt is pressed during the filling operation against the vent hole and it closes same. The valve plate of the filling valve is connected in this case directly with the outer sleeve of the anesthetic bottle via the pins. When the anesthetic bottle is pushed completely into the mounting hole of the filling device and the bottle valve opens, the valve plate reaches the end stop and the closing bolt is in contact by its flat packing with the vent hole. When the anesthetic bottle is pulled somewhat out of the filling device after the filling, the position of the valve plate changes as well, and the pressing force exerted by the closing bolt on the vent hole decreases until the vent hole is finally opened. The bottle valve will have already closed by that point in time, so that excess anesthetic can still be taken up from the filling device in the anesthetic tank. The valve plate, which is rigidly coupled with the outer sleeve of the anesthetic bottle, is used to release the vent hole via the closing bolt when the bottle valve of the anesthetic bottle has just closed.

An exemplary embodiment of the present invention is shown in the drawings and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENTS

Figure 1:
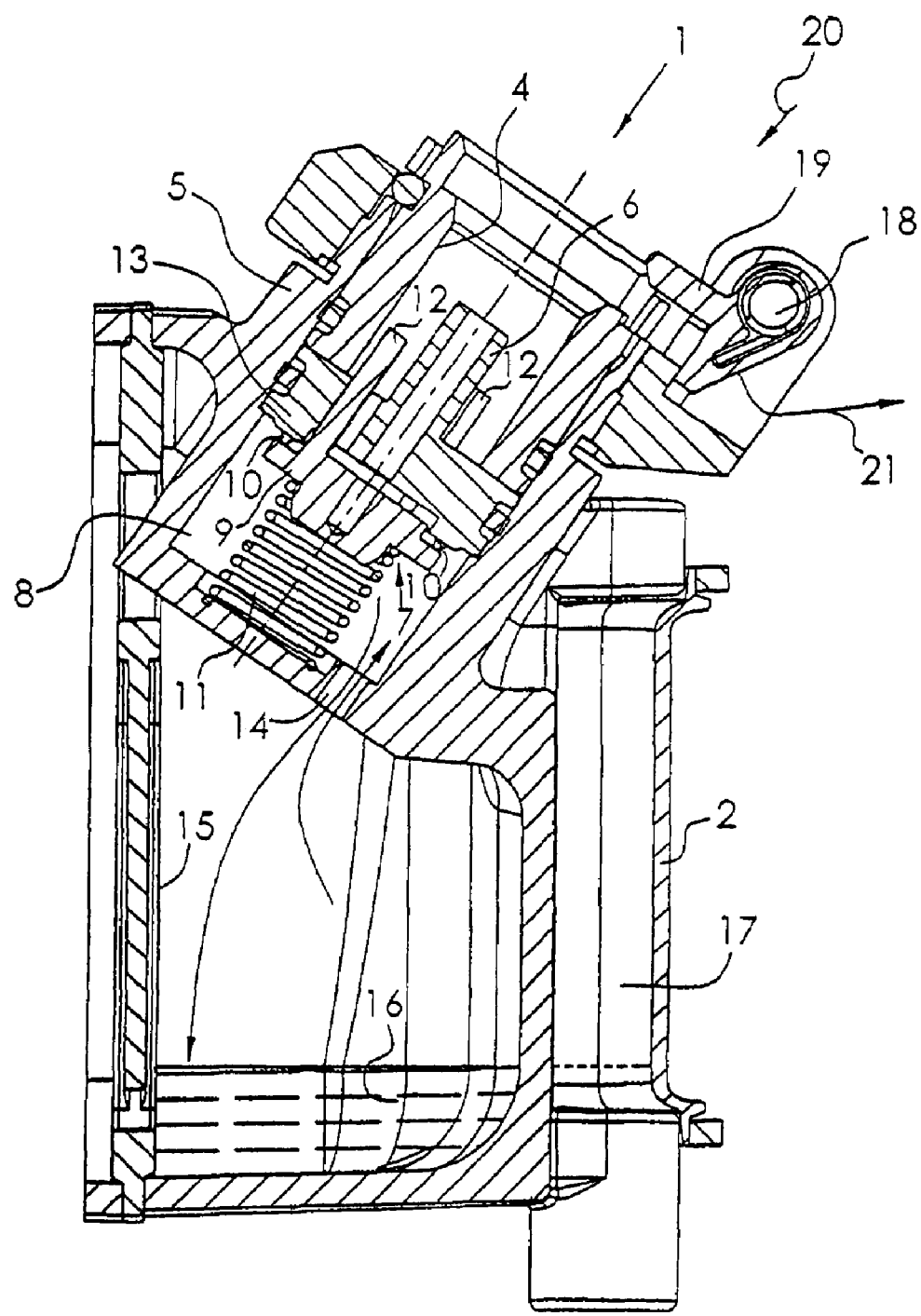
FIG. 1 is a longitudinal sectional view through a filling device according to the state of the art.

Referring to the drawings in particular, FIG. 1 schematically illustrates a filling device 1 according to the state of the art at an anesthetic evaporator 2, which is not shown more explicitly. The filling device 1 comprises a mounting hole 4 with a tubular inner part 6 fixed in a valve housing 5. A filling valve 7, which is arranged in a valve chamber 8 under the inner part 6, contains a valve plate 9, a sealing crater 10 and a valve spring 11, which presses the valve plate 9 against the sealing crater 10. Three pins 12 connected rigidly with the valve plate 9 pass through a mounting plate 13 of the inner part 6 and into the mounting hole 4. The valve chamber 8 is connected via a fluid channel 14 with an anesthetic tank 15 for receiving liquid anesthetic 16. The filling level of the anesthetic 16 in the anesthetic tank 15 can be read on a viewing glass 17. A bar 19, which is pivotable around a bolt 18, is pretensioned with a spring and is displaceable along the arrows 20, 21 and snaps back into the starting position shown in FIG. 1 under the action of the spring force, is fastened on the top side of the filling device 1.

Figure 2:
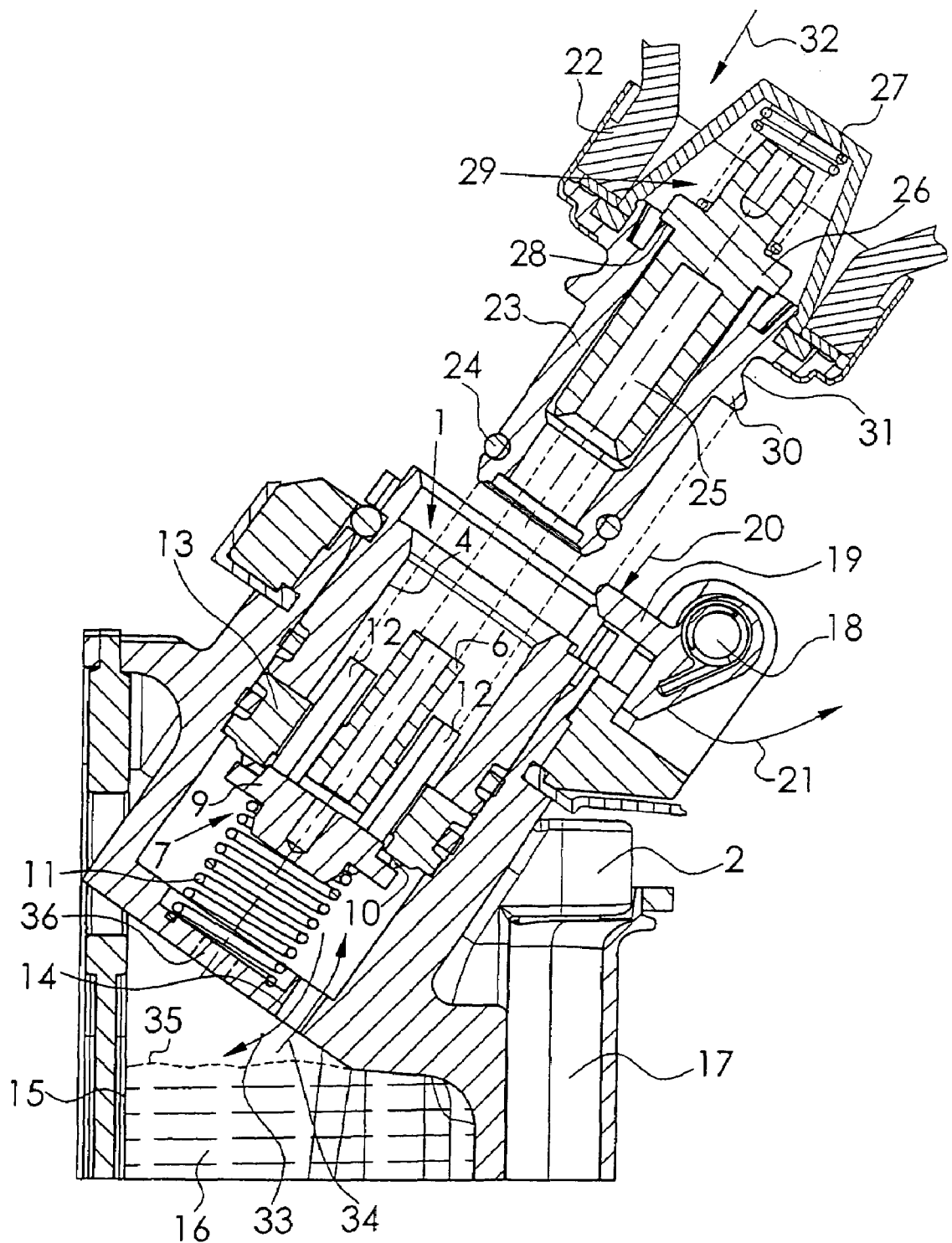
FIG. 2 is a longitudinal sectional view of a filling device according to FIG. 1 also showing a vent hole according to the invention in combination with an anesthetic bottle.

FIG. 2 shows the filling device 1 according to FIG. 1 with an anesthetic bottle 22. Identical components are designated by the same reference numbers as in FIG. 1. The anesthetic bottle 22 has an outer tube 23 with an O-ring 24, which can be inserted into the mounting hole 4 of the filling device 1, and an inner tube 25, which is located within the outer tube 23 in such a way that it can perform a lifting motion. The inner tube 25 is provided on its side facing the anesthetic bottle 22 with a valve disk 26, which is pressed against a valve seat 28 by means of a valve spring 27. The valve disk 26, the valve seat 28 and the valve spring 27 together form a bottle valve 29.

When the anesthetic bottle 22 is not inserted into the filling device 1, the valve spring 27 presses the valve disk 26 against the valve seat 28 and the bottle valve 29 is closed.

The filling operation takes place as follows.

The outer tube 23 is first inserted into the mounting hole 4, and the outer tube 23 in the mounting hole 4 is sealed with the O-ring 24. The front side of the outer tube 23 will then engage the pins 12, and the valve plate 9 is lifted off from the sealing crater 10. The filling valve 7 is opened. The bottle valve 29 of the anesthetic bottle 22 is still closed at this point in time.

A projecting bead 30, which is arranged at the outer tube 23, will later engage the bar 19 and press same downward along the arrow 20. When the bar 19 has reached the top side 31 of the bead 30, the bar 19 snaps back into the starting position shown in FIG. 2 and secures the anesthetic bottle 22 within the filling device. The bottle valve 29 is still closed at this point in time. By pressing the anesthetic bottle 22 along arrow 32, the outer tube is pushed deeper into the mounting hole 4 and the stationary inner part 6 will engage the inner tube 25, as a result of which the bottle valve 29 opens and anesthetic flows into the anesthetic tank 15 via the fluid channel 14 along arrow 33. Anesthetic vapor enters the anesthetic bottle 22 along arrow 34 in the opposite direction. The anesthetic tank 15 and the anesthetic bottle 22 are connected with one another in the form of communicating vessels. The filling operation is continued until the liquid level 35 of the anesthetic 16 has reached the level of the fluid channel 14 and the exchange of gas between the anesthetic tank 15 and the anesthetic bottle 22 is no longer possible. If the anesthetic bottle 22 is released, the bottle valve 29 closes. It may happen because of the fluid channel 14 being closed by the liquid level 35 that a residual amount of anesthetic 16 that has been left in the mounting hole 4 cannot flow off into the anesthetic tank 15 any longer.

An additional vent hole 36, which is opened with a vent valve not specifically shown in FIG. 2 immediately after the closing of the bottle valve 29 in order for an additional volume of anesthetic 16 to be able to be taken up by the anesthetic tank 15, is provided according to the present invention above the fluid channel 14. The vent hole 36 is indicated in FIG. 2 by broken lines only for the sake of greater clarity.

Figure 3:
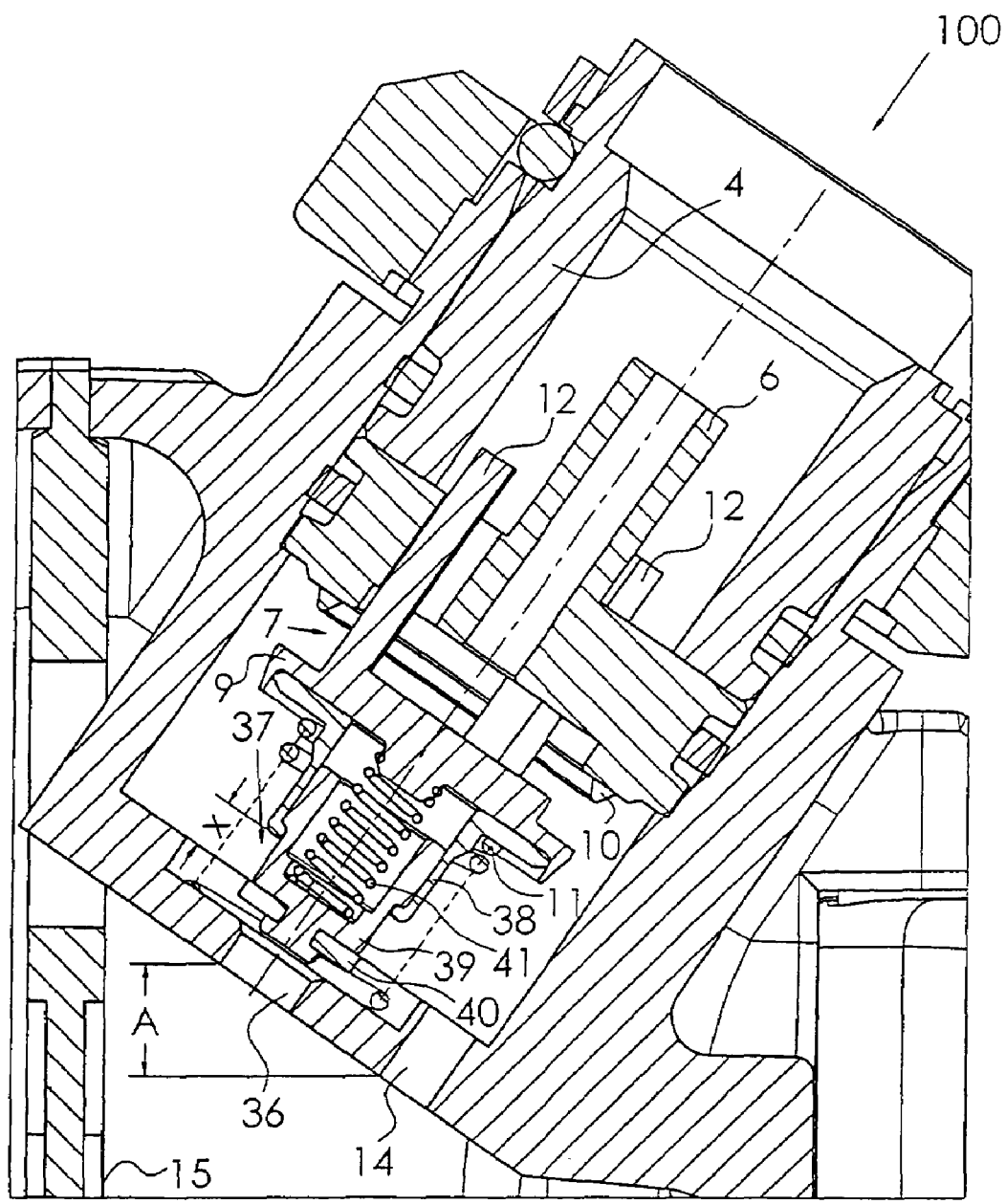
FIG. 3 is a longitudinal section of a filling device according to the present invention.

FIG. 3 shows a filling device 100 according to the present invention, in which the vent valve 37 with the vent hole 36 is arranged under the valve plate 9. Identical components are designated by the same reference numbers as in FIGS. 1 and 2. The valve spring 11 is not shown completely in FIG. 3 for the sake of greater clarity.

The vent valve 37 comprises a sleeve 38 and a closing bolt 39, which is accommodated therein in such a way that it can perform lifting motions, with a flat packing 40. The closing bolt 39 is braced with a spring 41 in relation to the sleeve 38 and can be displaced by the amount x in relation to the sleeve 38.

FIG. 3 shows a valve position of the vent valve 37, in which the anesthetic bottle 22, of FIG. 2, is still located within the mounting hole 4, in which the bottle valve 29 is, however, already closed. Excess anesthetic can flow off into the anesthetic tahk 15 via the fluid channel 14 through the opened vent hole 36. The anesthetic tank 15 can now take up a larger volume of anesthetic due to the vent hole 36 being located at a higher level by the amount "A."

Figure 4:
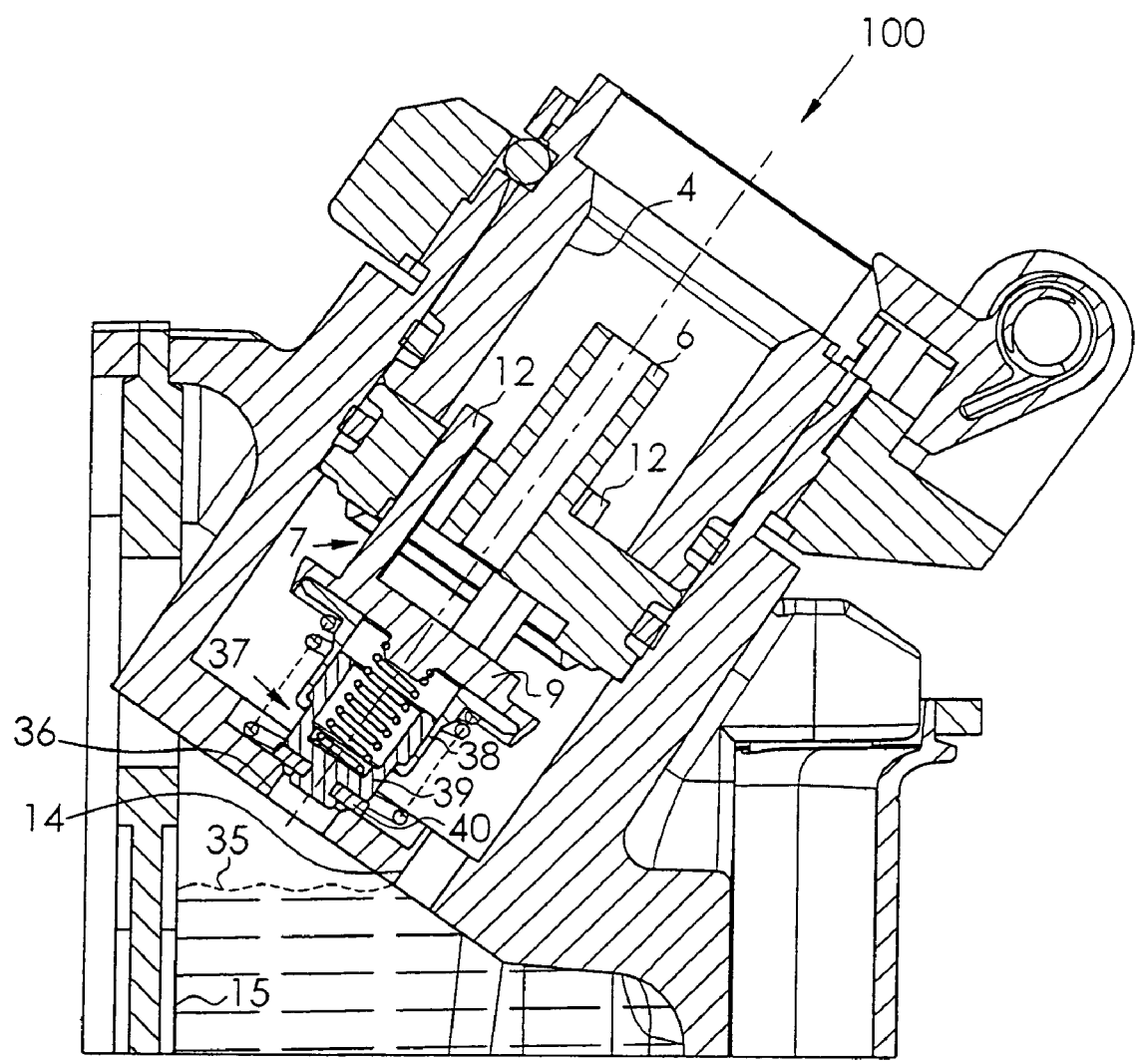
FIG. 4 is a longitudinal sectional view the filling device according to FIG. 3 during the filling operation.

FIG. 4 illustrates the filling device 100 during filling, in which the outer tube 23 of the anesthetic bottle 22, FIG. 2, has been pushed completely into the mounting hole 4 and the bottle valve 29 is opened by the inner part 6. In this position of the valve plate 9 at the end stop, the flat packing 40 closes the vent hole 36, and the closing bolt 39 is displaced within the sleeve 38 in the direction of the valve plate 9. The liquid level 35 within the anesthetic tank 15 can rise now only up to the level of the fluid channel 14.

Figure 5:
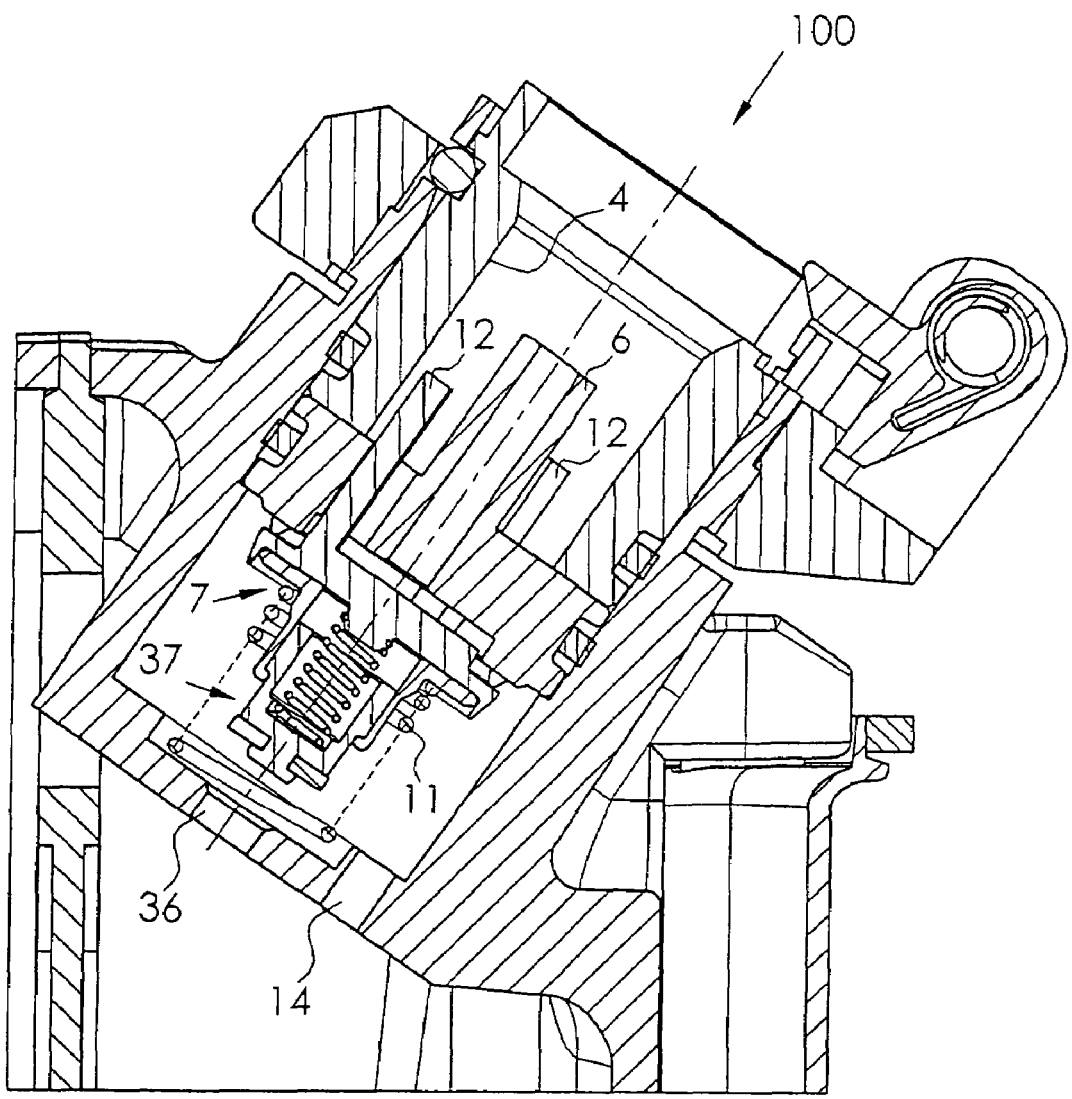
FIG. 5 is a longitudinal sectional view of the filling device according to FIG. 3 after the removal of the anesthetic bottle.

FIG. 5 shows the filling device 100 with the anesthetic bottle 22 completely removed. The filling valve 7 is closed, and the fluid channel 14 and the vent hole 36 are opened.

While a specific embodiment of the invention have been shown and described in detail to illustrate the application of the principles of the invention, it will be understood that the invention may be embodied otherwise without departing from such principles.

What is claimed is:

1. A filling device for an anesthetic evaporator, which receives a connection device of an anesthetic bottle, the filling device comprising:
   a filling valve, which is intended to open or close as needed, wherein the anesthetic bottle and an anesthetic tank of the anesthetic evaporator are connected with one another during the filling operation in the form of communicating vessels via a fluid channel that can be closed by the liquid level of the anesthetic in the anesthetic tank;
   a vent hole, which can be opened or closed as needed, said vent hole being located above the fluid channel, said vent hole defining means for filling the anesthetic tank with an additional volume of anesthetic, the vent hole being located above the liquid level of said fluid channel; and
   a vent valve which opens or closes the vent hole, said vent valve being actuated via the filling valve in such a way that it can perform lifting motions such that it is switched into the open position immediately after the filling operation and is switched into the closed position during the filling operation, wherein the vent valve has a spring-loaded closing bolt, which is telescopically displaceable in relation to a valve plate of the filling valve and opens or closes the vent hole.

2. A process for filling an anesthetic evaporator with an anesthetic bottle via a filling device at the anesthetic evaporator, the process comprising the steps of:
   inserting a connection device of the anesthetic bottle into a mounting hole at the filling device to open a filling valve at the filling device to provide an anesthetic flow path from the anesthetic bottle to an anesthetic tank of the anesthetic evaporator through a mounting hole space on an anesthetic tank side of the filling valve and through a fluid channel and an anesthetic vapor return path from the anesthetic tank to the anesthetic bottle through the fluid channel and through the mounting hole space on the anesthetic tank side of the filling valve;
   introducing anesthetic from the anesthetic bottle into the anesthetic evaporator anesthetic tank via the fluid channel at the filling device with the anesthetic tank of the anesthetic evaporator and the anesthetic bottle connected with one another during the filling operation in the form of communicating vessels in which anesthetic flows from the anesthetic bottle to an anesthetic tank of the anesthetic evaporator through the mounting hole space on the anesthetic tank side of the filling valve and through the fluid channel and the anesthetic vapor passes from the anesthetic tank to the anesthetic bottle through the fluid channel and through the mounting hole space on the anesthetic tank side of the filling valve;
   closing the anesthetic flow path and the fluid channel by the liquid level in the anesthetic tank reaching a predetermined level precluding the anesthetic vapor from passing from the anesthetic tank to the anesthetic bottle through the fluid channel so as to preclude anesthetic from flowing from the anesthetic bottle to an anesthetic tank;
   providing a vent hole above a fluid level of the anesthetic tank at the fluid channel; and
   opening the vent hole to provide fluid communication between the anesthetic tank and the mounting hole space on the anesthetic tank side of the filling valve needed such that an additional volume of liquid, which is above the liquid level of the fluid channel, is filled into the anesthetic tank through the fluid channel based on a venting of anesthetic vapor from the anesthetic tank to the mounting hole space on the anesthetic tank side of the filling valve.

3. A process in accordance with claim 2, further comprising opening the vent hole immediately after the conclusion of the filling program in order to drain off excess anesthetic from the filling device into the anesthetic tank.

4. An anesthetic evaporator filling system, comprising:
   an anesthetic supply bottle with a connection device;
   an anesthetic tank with structure defining a fluid channel that can be closed by the liquid level of the anesthetic in the anesthetic tank and a vent hole, said vent hole being located at a level above the fluid channel;
   a filling device with structure defining a mounting hole and a filling valve opened by the connection of said anesthetic bottle and said filling device with one another during a filling operation to provide communicating vessels, said filling device having a mounting hole space on an anesthetic tank side of said filling valve wherein anesthetic in the anesthetic supply bottle flows into the anesthetic tank via said mounting hole space and said fluid channel and anesthetic vapor passes from the anesthetic tank to the anesthetic bottle through said mounting hole space and said fluid channel; and
   a vent valve which assumes an open vent hole position or a closed vent hole position, said vent valve being actuated via the filling valve to switch into an open position immediately after the filling operation to allow anesthetic vapor communication from said anesthetic tank to said mounting hole space thereby allowing anesthetic to flow into said anesthetic tank from said mounting hole space and being switched into the closed position during the filling operation.

5. An anesthetic evaporator filling system in accordance with claim 4, wherein the vent valve has a spring-loaded closing bolt, which is telescopically displaceable in relation to a valve plate of the filling valve and opens or closes the vent hole.

6. A filling device for an anesthetic evaporator, which receives a connection device of an anesthetic bottle, the filling device comprising:
   a valve housing;
   a filling valve in said valve housing;
   an anesthetic tank for holding anesthetic, said valve housing having a mounting hole space on an anesthetic tank side of said filling valve with a fluid channel providing a fluid path between said mounting hole space and said anesthetic tank and a vent hole providing a fluid path between said mounting hole space and said anesthetic tank fixed at a level above a level of said fluid channel, whereby the anesthetic bottle and the valve housing are connected with one another during a filling operation opening said filling valve to provide communicating vessels in which anesthetic flows from the anesthetic bottle to an anesthetic tank through the mounting hole space and through the fluid channel and anesthetic vapor passes from the anesthetic tank to the anesthetic bottle through the fluid channel and through the mounting hole space.

7. A filling device in accordance with claim 6, further comprising:

a vent valve cooperating with said vent hole to assume an open vent hole position or a closed vent hole position, said vent valve being actuated via the filling valve to switch into an open position immediately after the filling operation to allow anesthetic vapor communication from said anesthetic tank to said mounting hole space thereby allowing anesthetic to flow into said anesthetic tank from said mounting hole space and being switched into the closed position during the filling operation.

8. An anesthetic evaporator filling system in accordance with claim 7, wherein said vent valve has a spring-loaded closing bolt, which is telescopically displaceable in relation to a valve plate of the filling valve and opens or closes the vent hole.

* * * * *